(12) United States Patent
Aykol et al.

(10) Patent No.: US 11,610,652 B2
(45) Date of Patent: Mar. 21, 2023

(54) AUTONOMOUS INORGANIC MATERIAL SYNTHESIS MACHINE

(71) Applicant: Toyota Research Institute, Inc., Los Altos, CA (US)

(72) Inventors: Muratahan Aykol, San Jose, CA (US); Santosh K. Suram, Mountain View, CA (US)

(73) Assignee: Toyota Research Institute, Inc., Los Altos, CA (US)

( * ) Notice: Subject to any disclaimer, the term of this patent is extended or adjusted under 35 U.S.C. 154(b) by 366 days.

(21) Appl. No.: 16/868,037

(22) Filed: May 6, 2020

(65) Prior Publication Data

US 2021/0350881 A1    Nov. 11, 2021

(51) Int. Cl.
G16C 20/10 (2019.01)
G16C 20/80 (2019.01)
G16C 20/90 (2019.01)
G16C 60/00 (2019.01)

(52) U.S. Cl.
CPC ............. *G16C 20/10* (2019.02); *G16C 20/80* (2019.02); *G16C 20/90* (2019.02); *G16C 60/00* (2019.02)

(58) Field of Classification Search
CPC ......... G16C 20/10; G16C 60/00; G16C 10/00
See application file for complete search history.

(56) References Cited

U.S. PATENT DOCUMENTS

| 9,962,677 B2 | 5/2018 | Cronin | |
| 2011/0106794 A1* | 5/2011 | Hori | G16C 20/10 707/723 |
| 2021/0065851 A1* | 3/2021 | Madrid | G16C 10/00 |

FOREIGN PATENT DOCUMENTS

EP    1002572 A2    5/2000

OTHER PUBLICATIONS

Gromski, P. et al., "Universal Chemical Synthesis and Discovery with 'The Chemputer'," Trends in Chemistry, Jan. 2020, vol. 2, No. 1, 9 pages.
Bedard, A. et al., "Reconfigurable system for automated optimization of diverse chemical reactions," Science 361, 1220-1225 (2018).
Duros, V. et al., "Intuition-Enabled Machine Learning Beats the Competition When Joint Human-Robot Teams Perform Inorganic Chemical Experiments," J. Chem. Inf. Model. 2019, 59, 2664-2671.

* cited by examiner

*Primary Examiner* — Lam S Nguyen

(74) *Attorney, Agent, or Firm* — Christopher G. Darrow; Darrow Mustafa PC

(57) ABSTRACT

A synthesis machine for preparation of a targeted inorganic material for recommended synthesis by a computer program that determines optimal solid-state methods for synthesis of an inorganic material. The computational method involves inputting a target inorganic material, querying structural data and thermodynamic data for the target inorganic material, enumerating possible synthetic reactions to construct a synthetic reaction database with a viable subset of the possible synthetic methods. The routine generates a nucleation metric and competition metric that are combined to provide recommended synthetic methods. The output for each of the recommended syntheses are input into a robotic synthesis machine where the delivery of reactants, reaction conditions, and analysis of extent of reaction, and product quality is controlled by a processor.

17 Claims, 6 Drawing Sheets

AUTONOMOUS INORGANIC MATERIAL SYNTHESIS MACHINE

TECHNICAL FIELD

The present disclosure generally relates to a robotic solid-state inorganic material synthesis where the instructions for synthesis and analysis are provided from computer output that determines optimal solid-state synthetic methods for synthesis of a target inorganic material.

BACKGROUND

The background description provided herein is for the purpose of generally presenting the context of the disclosure. Work of the presently named inventors, to the extent it may be described in this background section, as well as aspects of the description that may not otherwise qualify as prior art at the time of filing, are neither expressly nor impliedly admitted as prior art against the present technology.

Synthesis design for crystalline inorganic materials of a targeted polymorphic form is extremely challenging, particularly for solid-state synthesis from available reactants either starting materials or precursors. Computational systems for design of organic small molecule synthesis (e.g. in drugs design) have been realized and implemented (e.g. retrosynthetic analysis) from databases available and/or generated sets of known solution reactions that can be incrementally applied to achieve a target molecule. No such broad and computationally accessible reaction selection and prioritization strategy and method currently exists for crystalline inorganic solid materials.

The number of combinatorial possibilities of crystal structures and compositions that define the space of inorganic materials is enormous and the resulting number of polymorphic forms for any single material composition further adds to the challenge of designing structures that achieve desired properties and their synthesis from available inorganic materials. Given the massive number of possibilities for materials and synthetic routes that could lead to their formation, the design process is well suited to the ability of computer algorithms to consider from the possibilities in a time frame that is rather inconceivable for strictly human inspection and design. Hence, a system and method to identify viable and efficient synthetic routes that provide access to new inorganic materials or polymorphs or alternative routes for existing/known inorganic materials or polymorphs is desirable. The ability of such a system to input information for targets and starting materials or precursors to these targets from available material structure and thermochemistry databases and output the synthetic methods in solid-state laboratory synthesis experiments and/or for use with robotic systems for the synthesis of the products is desirable.

Systems that screen a wide array of inorganic compounds have been examined for the discovery of new materials. These efforts have been directed to discovery and optimization of materials, such as superconductors, zeolites, magnetic materials, phosphors, nonlinear optical materials, thermoelectric materials, and high and low dielectric materials. These methods have been focused on simultaneous formation and testing of arrays of materials with systematic differences in their nominal composition, typically where an array of different compounds with some common elements are formed by site specific delivery of chemicals and a common processing of all sites simultaneously followed by an analysis on each of the sites for some desired property and verification of the compound formed, without any robust or strategic control over the which compounds and/or what polymorphic compounds appear in the process. The coupling of an artificial intelligence process for identification of a synthesis design to a target inorganic material with a targeted polymorphic form by a solid-state synthesis from available reactants coupled with robotic preparation that can control and analyze the transformation and the product is desirable.

SUMMARY

This section provides a general summary of the disclosure and is not a comprehensive disclosure of its full scope or all its features.

In various aspects, the present teachings provide a synthesis machine for preparation of a target inorganic material where a synthesis planner module interfaced with a processor takes a user specified target inorganic material as input and outputs from a recommender computer program at least one solid-state synthetic method for the preparation of the target inorganic material that includes recommended syntheses from a viable subset of a multiplicity of possible synthetic reactions. In outputting the recommended syntheses routes for the target inorganic material, the synthesis planner module instructs the recommender computer program to consider starting materials/precursors available in its reactant storage inventory. The synthesis machine has at least one reaction vessel for containment of reactant(s) for formation of the target inorganic material. Each reaction vessel is for the performance of a single solid-state synthetic method under a first stoichiometry and first set of conditions contained in the output of the computer program or an specified stoichiometry and specified set of conditions modified according to a result of a previous preparation of the target inorganic material by the synthesis machine, and ultimately resulting from the first stoichiometry and first set of conditions. The synthesis machine has at least one delivery mechanism to provide a plurality of reactants to the reaction vessel in a quantity provided at the first stoichiometry or in the enumerated stoichiometry. The synthesis machine has at least one controller configured: to control the first or enumerated set of conditions required for the solid-state synthetic method; to monitor the first or enumerated set of conditions during the solid-state synthetic method; and to evaluate the progress of a reaction of the solid-state synthetic method.

In other aspects, the present teachings provide a method of synthesizing a target inorganic material by: receiving input for a target inorganic material, and requesting and receiving one or more recommended synthesis routes for the target inorganic material from a computational method through an interface with a synthesis planner module coupled to a processor; transferring at least one reactant and any desired diluent and catalyst to a reaction vessel in a quantity prescribed by a computer program; and imposing, under computer control, a temperature, pressure, over gas, and/or radiation as prescribed by the computer program to the reaction vessel. The reaction conditions are monitored under computer control. The extent of a reaction to the product inorganic material is determined using a set of sensors/probes with an output to the processor, which is then used by the synthesis planner to define the next actions in the system, such as to halt a reaction, alter reaction conditions, or initiate mechanical mixing/grinding, or calorimetric or other probe measurements. The formation and subsequent purity of the product inorganic material is determined by at least one analytical technique that is controlled by the processor of the synthesis planner. Subsequent reactions in a multistep synthesis are carried out with transferring of additional reactants, imposing conditions, monitoring the extent of the reaction, and determining the purity of the product for each reaction in the multistep synthesis, where such intermediate products can be stored in a staging area with an inert atmosphere for use in downstream reaction steps. Ultimately the target inorganic material is isolated in a manner controlled by the computer and delivered to the user.

In an aspect, the present teachings provides a non-transitory computer-readable medium for synthesizing a target inorganic material and storing instructions that, when executed by one or more processors, cause the one or more processors to receive input for a recommended synthesis for a target inorganic material from a computational method for determining the recommended synthesis through an interface with a processor. Subsequently, the computer program prescribes the transfer at least one reactant and any desired diluent and catalyst to a reaction vessel. Reaction vessel conditions, including temperature, pressure, over gas, and/or radiation, are imposed as prescribed by the computer program. At least one reaction condition is monitored as directed by the computer program. The extent of reaction is followed by sensors/probes output to the processor, and the formation and subsequent purity of the product inorganic material is determined by at least one analytical technique controlled by the processor. A synthesis planner module keeps track of this phase formation and purity information received through the processor to decide on to trigger possible actions from a list of actions, including an intermediate grinding and reheating, enumeration or adjustment of conditions, such as temperature, pressure, and gas flow rate, requesting ex-situ calorimetric measurements for some or all of the reactants, and so on, via a controller coupled to its processors and robotic sample transporters as needed. The synthesis planner further makes the decision based on above-mentioned feedback from the probes/sensors to halt and/or alter the synthesis reaction to another reaction recommended as viable by the recommender system. The steps for each reaction can be repeated for each intermediate product that is required in a multistep synthesis, and such intermediates can be stored in an atmosphere controlled and/or inert staging area. Ultimately, the target inorganic material is isolated under computer control and delivered to the user.

Further areas of applicability and various methods of enhancing the above coupling technology will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein.

Figure 1:
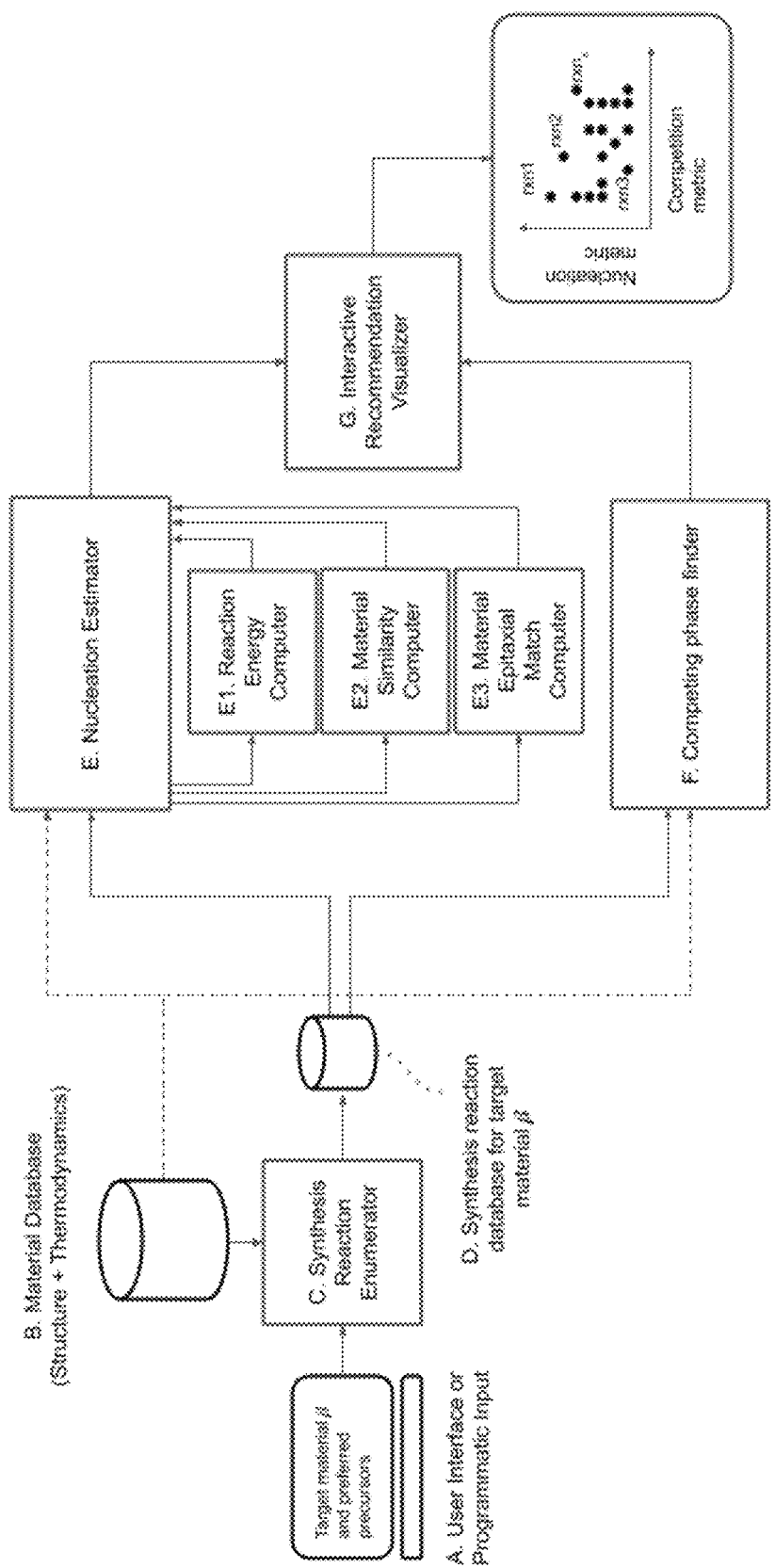
FIG. 1 shows a flow chart for an inorganic synthesis identifying routine from the input of a target inorganic material β, through the output of recommendations for the synthesis of β.

It should be noted that the figures set forth herein are intended to exemplify the general characteristics of the methods, algorithms, and devices among those of the present technology, for the purpose of the description of certain aspects. These figures may not precisely reflect the characteristics of any given aspect and are not necessarily intended to define or limit specific embodiments within the scope of this technology. Further, certain aspects may incorporate features from a combination of figures.

DETAILED DESCRIPTION

The present teachings provide a synthesis machine to prepare target inorganic materials, which is interfaced with an empirical and computational data-driven framework from which solid-state synthetic methods are recommended for an input target inorganic material selected for preparation. The input material allows inspection and input from material databases to establish enumerated reaction stoichiometries that can form the target material and assess the best synthetic routes.

In such a synthesis machine, the input for forming a target inorganic material is taken by a synthesis planner module coupled to a component inorganic synthesis identifying routine for the delivering of the identified inorganic reactants and any catalysts, their combining as solids and gases, and recovering the target inorganic material. The synthesis machine can be fully automated and can include components for analysis. The analytical components can verify the identity of reactants, their thermal (calorimetric) properties, follow the extent of the reaction, and keep track of formation of, and verify the structure and composition of the target inorganic material. Other components can be included to monitor and control a temperature profile, impose and measure the pressure, and provide, as needed, the source of any reactive or inert over gas, heat, or pressure required. The scale of the synthesis would generally be in centigrams or less such that all synthesis meeting the imposed degree of recommendation can be assessed in a relatively short period of time and any given synthetic method can be optimized for any advantageous deviation from the recommended stoichiometry and physical conditions provided by the component inorganic synthesis identifying routine, where the changes are programmatic or imposed through a user interface.

The present teachings provide a synthetic machine that carries out inorganic synthesis identified by a routine that allows a user or programmed input of a desired end and/or beginning of a synthetic procedure, where a preferred reactant/precursor and/or a desired target inorganic material, although, generally, a product target inorganic material is input. As disclosed herein, the identified target inorganic material is one anticipated to achieve a function required for a product or method needed by the user although it could be from the position of a reactant supplier whose goal is the generation of a cornucopia of downstream products, where after identification of the target products, identification of the synthesis is needed to produce the target product. The programmed input can be from a routine that identifies inorganic materials that possess some desired property or structure.

The synthetic machine commences with the reception of a procedure after a computational determination of a viable subset of synthetic procedures to prepare a target inorganic material. The computational method is detailed below.

The input target inorganic material is received by a synthesis planner module, which identifies the possible reactants, the starting materials or precursors, available in the inventory of the synthesis machine and instructs the recommendation computer program to deliver a set of recommended viable synthesis routes for the synthesis of the target material considering also the presence of available reactants. In the recommendation computer program, an interface (A) commences an analysis of possible synthetic strategies, as is illustrated in FIG. 1. The primary input of the target is provided to a reaction enumerator (C), where all balanced reactions from all possible reactants to the target inorganic material are enumerated.

As indicated in FIG. 1, the enumerator (C) queries and receives input from a database of materials (B). The database is of structural and/or thermochemical data that can be of empirical thermodynamic data, which is tabulated or otherwise readily retrieved, or from first-principle computations, such as that available on the world wide web from Materials Project, Open Quantum Materials Database, AFLOW database, or is calculated within the domain of the processor or accessible computation systems that is used for the enumeration. If specified as a condition by the user, elements that may not necessarily be a component in the target but are generally abundant in common starting materials/precursors such as C, N, O, H, etc. can be included in reactant querying from databases hence allowing different subclasses of starting materials/precursors such as carbonates, nitrates, hydroxides etc. to be included as part of possible reactants, and reactions including such reactants can be balanced by allowing the release of the added element along with the target as a removable byproduct, often in gas form, such as CO, $CO_2$, $H_2O$, or $NO_2$. The enumerator can also store the thermodynamic properties of the products and reactants acquired from materials databases for the balanced equations in database (D) to later provide to downstream modules. The enumeration can include those for transformations from readily available starting materials to the reactants (or intermediates) used as input for the reaction enumerated, hence, a plurality of transformations from starting materials through intermediates to the target inorganic material can be conducted. The output of the reaction enumerator can be stored in a synthesis database (D) in a computationally accessible form.

Each of the enumerated reactions from the synthesis reaction database (D) can be delivered to two computational subsystems that perform as a nucleation estimator (E) and as a competing phase finder (F). These two subsystems are programmed to query and retrieve thermochemical data as needed from the database of materials (B) or access that date via the reaction database (D). The two subprograms provide complementary information concerning the outcome and viability of the chemical transformation being calculated for the input provided by the synthesis database (D).

The nucleation estimator (E) carries out three series of calculations to estimate a metric proportional to the barrier of nucleation to a phase of target inorganic material β. E1 acquires thermodynamic data, including enthalpy and entropy data from the reaction database (D) and/or from material property database (B) for entries in reactions and, calculate the reaction energies, and can apply empirical corrections to calculated data to ensure the data's reliability. In calculating the reaction energy, often the enthalpy data is the major contribution from the solid phases and their entropy contribution can be neglected as a reasonable approximation, whereas entropy contribution is often non-negligible for gases at finite temperatures of interest and hence should be included and are available from standard thermodynamic tables/databases. E1 can apply such contributions of the user-specified thermodynamic conditions (such as temperature, gas pressure, etc.) using common thermodynamic formalisms to ensure those conditions are reflected in the calculated free energy of the synthetic reaction. E2 computes a similarity value for every reactant and the target inorganic material β from crystal structure information using either descriptors of the material composition and its crystal structure or crystal structure representation methods for each reaction stored in synthetic database (D). The similarity value can be obtained from an inverse dependence on a distance (such as Euclidean distance, Manhattan distance, Cosine distance, etc.) measured in a high-dimensional space provided by the input crystal structure data, where shorter distances result for similar materials and longer distances for dissimilar materials, and in turn similar materials have higher similarity values and dissimilar materials have lower similarity values. Alternatively, the similarity values could be obtained directly from similarity metrics such as Tanimoto similarity, Dice similarity, etc. An output similarity value is stored for each reactant and the target material β for all enumerated reactions in the synthetic database D. E3 finds epitaxially matching facets for the reactants and target inorganic material β from the calculated structures for every reaction in the synthetic database D that was generated. ++An epitaxial matching quantity can be generated as a minimal matching area or a derived score, materials that have matching epitaxial relationships (or minimal matching area for epitaxial matching) having a higher score compared to those that do not. Output from E1, E2, and E3 are used to compute a nucleation barrier related metric for each reaction that forms the target inorganic material β.

Computation of the nucleation barrier related metric begins from classical nucleation theory (CNT), where the rate of nucleation of a new phase β is proportional to two exponential terms expressed as:

$$\dot{N} \sim \exp(-\Delta G^*/kT) \cdot \exp(-\Delta E_d/kT), \quad \text{Eq. 1}$$

where $\Delta G^*$ is the critical energy barrier for nucleation and whose minimization favors nucleation. $\Delta E_d$ is a barrier term for transport of species that has a similar effect. The nucleation estimator (E) system searches reactions with small $\Delta G^*$ to the target inorganic material β to yield large nucleation rates. $\Delta G^*$ is minimized where nucleation is heterogeneous, that being on the surface of another material. Nucleation rates are at a maximum using reactants that have an optimal balance between bulk reaction energy $\Delta G_x$ (as computed in E1) and surface/interphase energy penalties, which is where the synthetic reaction has the smallest $\Delta G^*$ value. Depending on the targeted synthesis approach, as will be addressed below, $\Delta E_d$ is optionally included as a penalty term if transport can be a bottleneck of the synthesis of the target material.

Figure 2:
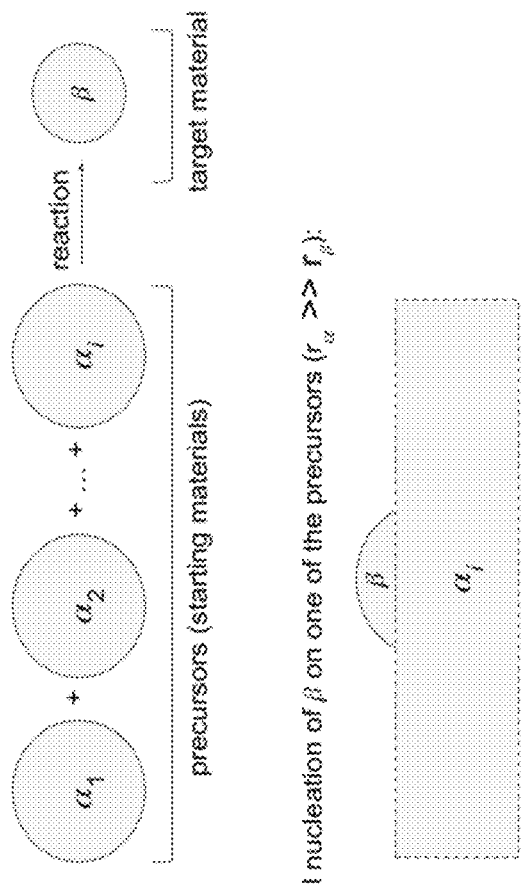
FIG. 2 shows for a plurality of synthetic methods how each is analyzed based on the initial nucleation of the target inorganic material β for each of the reagents.

The inorganic synthesis identifying program constrains the output to the target inorganic material β to those conditions where the synthesis happens in contact with at least one solid reactant (precursor) such that heterogeneous nucleation of β can take place on the reactant's surface. As illustrated in FIG. 2, each precursor $\alpha_i$ is identified and evaluated for nucleation of target β. For β nucleating on one of the precursors $\alpha_i$, evaluation is carried out using:

$$\Delta G^*[\beta \text{ on } \alpha_i] = 16\pi/3 \cdot \gamma_{\beta v}^3 / \Delta G_x^2 \cdot f[S(\beta \text{ on } \alpha_i)] \qquad \text{Eq. 2}$$

where $\Delta G_x$ is the bulk thermodynamic reaction energy for the transformation where one of the reactants is $\alpha_i$, which can be approximated as energy of synthesis reaction x per volume of β, that is obtained from the experimental and/or computational databases with high accuracy and/or from a database of materials and their properties (B) for each reaction stored in the synthetic database (D). Thermodynamic conditions input by the user (e.g. target temperature, gas pressure, etc.) can be accounted for in computation of $\Delta G_x$ as explained before. The term $\gamma_{\beta v}$ is the surface energy of target phase β (between β and vacuum or β in the synthesis environment) and is a property of the phase β only. For the synthetic architecture described here as governed by Eq. 2, the relative ranking of different synthesis reactions for their $\Delta G^*$ for β on $\alpha_i$ clearly does not depend on knowing an absolute value of $\gamma_{\beta v}$. Therefore, for a relative comparison of $\Delta G^*$ values pertaining to different synthetic reactions (and their constituent reactants $\alpha_i$), only factors that must be quantified or approximated are $\Delta G_x$ and the scaling factor: f[S (β on $\alpha_i$)].

As shown in FIG. 2, the initial formation of phase β occurs with nucleation on one of its reactants/precursors, $\alpha_i$. Any curvature of the precursor surface can be neglected, and the traditional equation of heterogenous CNT for a spherical cap on a flat surface can be used, where the term f can be described as:

$$f[S(\beta \text{ on } \alpha_i)] = (2 - 3S(\beta \text{ on } \alpha_i) + S(\beta \text{ on } \alpha_i)^3)/4 \qquad \text{Eq. 3}$$

Here $-1 \leq S(\beta \text{ on } \alpha_1) \leq 1$ and hence $0 \leq f[S(\beta \text{ on } \alpha_i)] \leq 1$. A small value of $f[S(\beta \text{ on } \alpha_i)]$ results in a low value of $\Delta G^*[\beta \text{ on } \alpha_i]$, which favors nucleation. The value of $S(\beta \text{ on } \alpha_i)$ relates to the surface and interfacial energies by the equation:

$$S(\beta \text{ on } \alpha_i) = (\gamma_{\alpha v} - \gamma_{\beta \alpha}) / \gamma_{\beta v}. \qquad \text{Eq. 4}$$

Absolute values of γ for all possible synthesis reactions are intractable to measure or compute. However, similar $\alpha_i$ and β structures, and such structures having matching epitaxial relationships can result in higher S values compared to other pairs, and can have S approaching 1 for highly similar and epitaxially matching structures (S→1), which results in a small f. This scenario allows the definition of the range of interest to be where $\gamma_{\alpha v}$ and $\gamma_{v \beta}$ are close, hence the similarity of structures, and $\gamma_{\beta \alpha}$ is as small as possible, hence similarity and epitaxial matching of structures. This allows an approximation of S defined in Eq. 4 as a deviation from its ideal value of 1 as:

$$S(\beta \text{ on } \alpha_i) \approx 1 - q(\beta, \alpha_i) \qquad \text{Eq. 5}$$

where $q(\beta, \alpha_i)$ is a function that approximates the deviation related to the degree of similarity and epitaxially-relatedness of β and $\alpha_i$, and q yields a positive value with the ideal value being 0 for exact similar/epitaxially matches of the β and $\alpha_i$ structures.

Standardized and/or normalized (to interval [0,1]) quantities of structural similarity and minimal epitaxial matching area can be used for epitaxial matching, namely $q_{sim}$ and $g_{epi}$ that are combined with equal weights to obtain q in Eq. 5.

Models can be used for calculation of actual values of γ. However, since reactant materials that can preferably nucleate the target relative to the others are the ones that system prefers and needs to identify, finding reactant materials that would maximize S, closer to 1 in the form $1 - q(\beta, \alpha_i)$, as above, is adequate for a data-driven reaction screening. Among the $S(\beta \text{ on } \alpha_i)$ values calculated for a given reaction corresponding to each reactant $\alpha_i$ the reaction has, the smallest S can be assigned to the reaction.

As indicated above, depending on the targeted synthesis approach, $\Delta E_d$ can be omitted or included if transport is considered as a bottleneck in synthesis of target β. If synthesis occurs in a way that facilitates transport the term can be omitted. Where transport is limited by the phases, being exclusively a solid-state reaction, inclusion is made using the approximation:

$$\Delta E_d \sim C \times q_{sim} \qquad \text{Eq. 6}$$

where, similar structures have a lower $\Delta E_d$ value and C is a constant, that is given a value such as 10 eV, which would yield a high transport barrier for dissimilar structures and a low transport barrier for similar structures. Here $q_{sim}$ pertaining to $\alpha_i$ whose S is assigned to the reaction, or a certain aggregation of $q_{sim}$ of all reactants (e.g. mean) van be used. These parameters can be further optimized.

The parameters $\Delta G^*$ and, optionally, $\Delta E_d$ are used to compute a metric $\Delta G_b$ which approximates a relative barrier to nucleation of the target material for each reaction:

$$\Delta G_b \sim \Delta G^* + \Delta E_d \qquad \text{Eq. 7}$$

The $\Delta G_b$ value serves as a nucleation barrier metric (in the light of Eq. 1) where lower values indicate more favorable nucleation of β. If user-specified thermodynamic conditions exist (temperature, pressure etc.) their effects can be included when data is available, particularly as part of reaction energy $\Delta G_x$ in $\Delta G^*$. As explained before, to a first approximation, entropy effects are neglected for solid compounds or elements. Entropy and enthalpy contributions, as controlled by temperature and pressure, are included from available tabulated data and common thermodynamic formalisms for gaseous molecules, such as $O_2$, $N_2$, $H_2$, $F_2$, CO, and $CO_2$, included in the balanced reactions. As a primary requirement, $\Delta G_x$ has to be negative under the given thermodynamic conditions for the reaction to progress and hence be considered as viable and passed to later stages; otherwise, the reaction is labeled as "not viable", and removed from further analysis.

Although maximizing nucleation rate is a focus for synthesis of a target inorganic material β phase, the same reactants can lead to nucleation of other phases than β and is not addressed by the computations to maximize the nucleation rate. Cross-phase comparison of nucleation rates for all possible products from a given set of reactants requires quantitative values for surface and interface energies and is impractical. For this reason, the competing phase finder F is employed.

Figure 3:
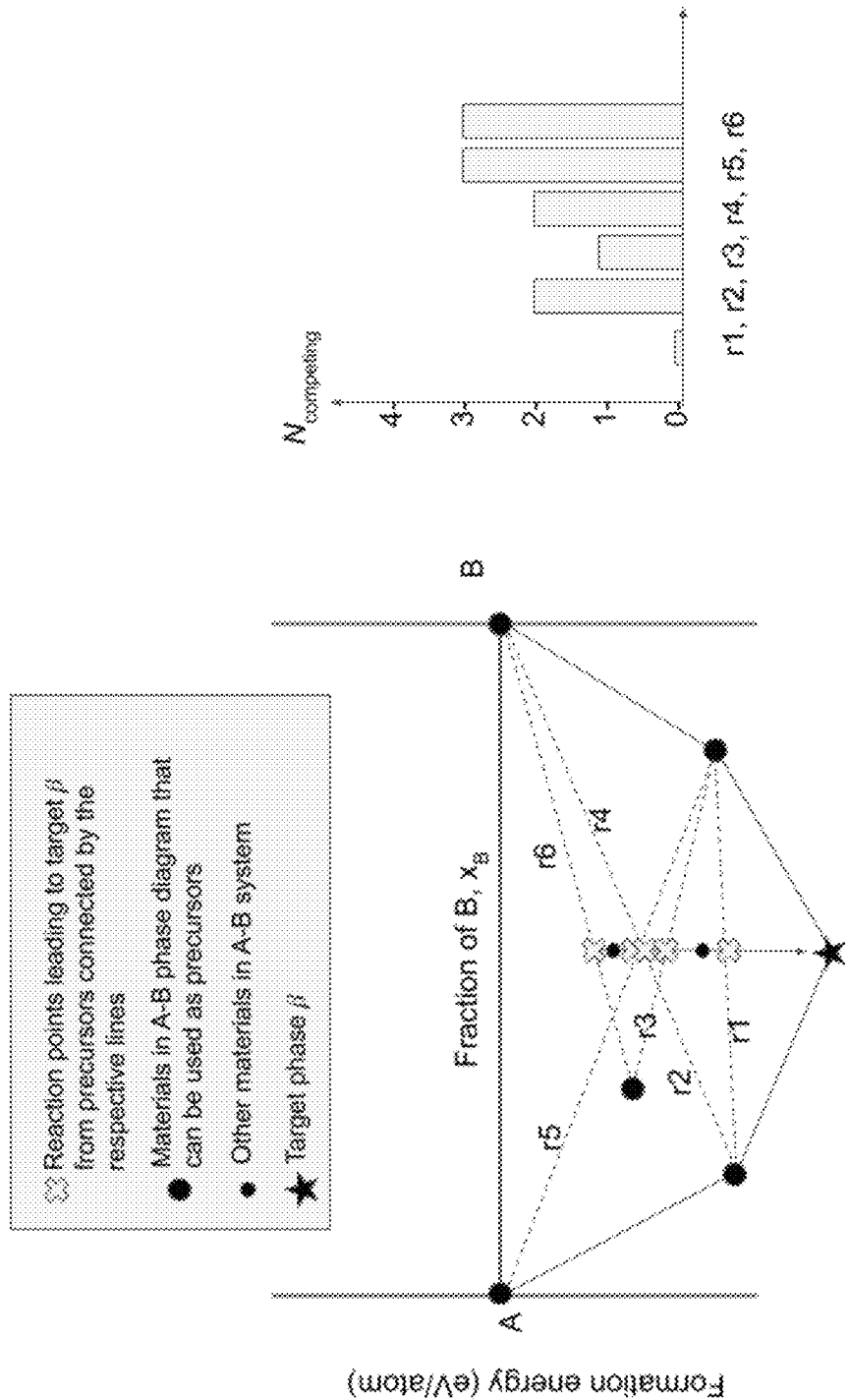
FIG. 3 is illustrative of an energy diagram for possible competing phases during a synthesis of a target inorganic material β and a bar graph of the numerated viable competing reactions.

In the competing phase finder F, a metric is computed that is the number of possible thermodynamically favorable competing phases ($N_{competing}$) for any synthesis reaction directed to the target phase inorganic material β. A viable competing phase requires a thermodynamically favorable reaction energy. Hence, from the reactants of a selected reaction for synthesis of the inorganic material β, the number of possible products, $N_{competing}$ that have viable (negative) reaction energies starting from the same reactants are enumerated, in the manner illustrated in FIG. 3. For consistency, reaction energies for competing phase finding are computed with the same process and conditions used for E1. A relatively larger value of $N_{competing}$ for a given reaction indicates a higher likelihood to yield impurities or other phases when the reaction is carried out, compared to other reactions that have smaller values of $N_{competing}$. Synthesis reactions that minimize the number of possible competing phases to the target inorganic material β are favored relative to others.

Figure 4:
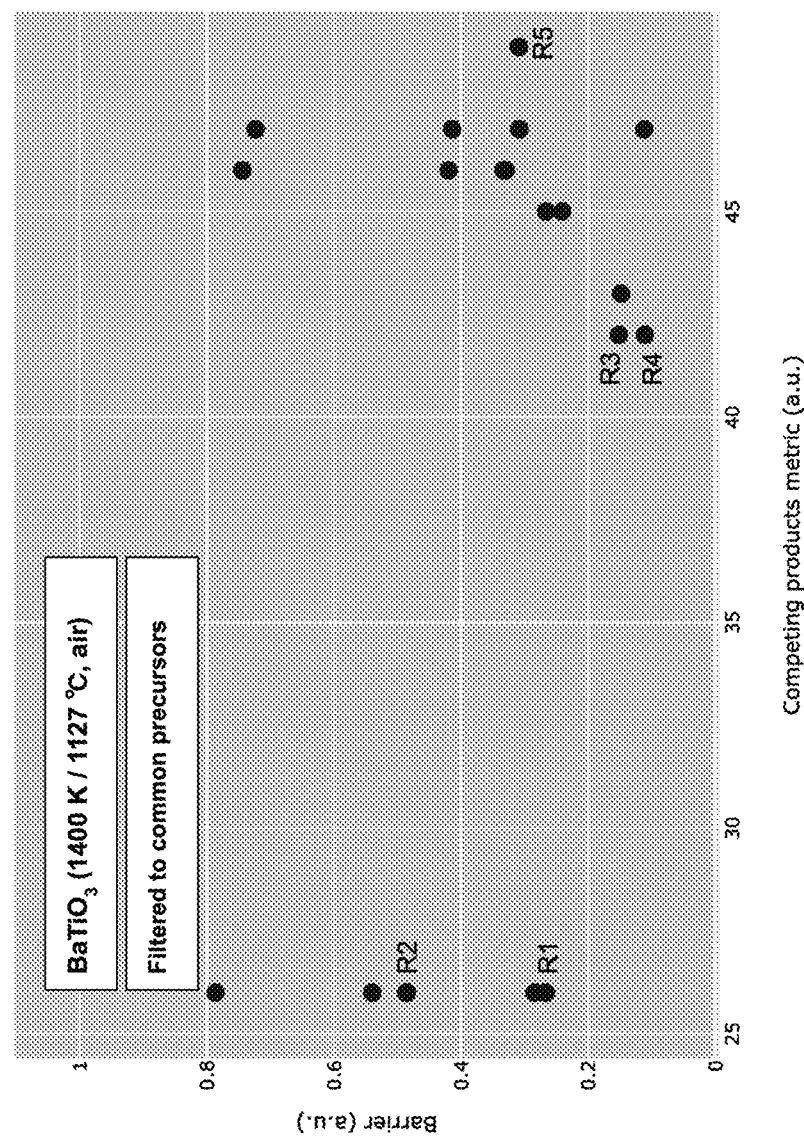
FIG. 4 is an exemplary output of the inorganic synthesis identifying routine for $BaTiO_3$ synthesis, where the recommended procedures are those nearest the origin of the plot or on or near the pareto frontier of the plot.

Ultimately, the inorganic synthesis identifying program produces a recommendation plot of possible synthesis reactions leading to the target inorganic material β in a recommendation visualizer (G) that can be an interactive recommendation visualizer, as shown in FIG. 1. These visualizations display the nucleation barrier and competition metrics for each synthesis reaction for the target phase, where a relatively smaller value for each indicates a relatively more favorable route. An example of such recommendation plots is shown in FIG. 4. The recommender plots can be interactive, where hovering over a point for a reaction displays information concerning the transformation. As smaller values are desired for the two independent metrics plotted on x and y axes, those reactions near or relatively close to the x-y origin and those forming or near the Pareto frontier of the scatter plot are the relatively more favorable reactions, and hence recommended to be prioritized in synthesis attempts based on the inorganic synthesis identifying program to produce the target inorganic material β. The inorganic synthesis identifying program results can be output as a Pareto optimal subset plot or can be configured to recommend the most viable point or points. The output recommended synthesis can be used as the input to a robotic synthesizer.

Figure 5:
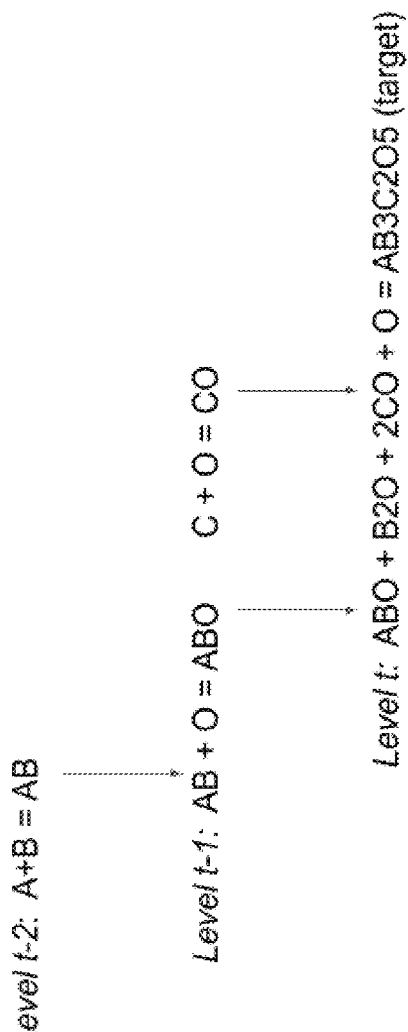
FIG. 5 is a plot of a progression of a multistep synthesis that can be calculated for consideration as a single recommendation where the recommended reactions to intermediate products are determined in addition to the final transformation.

The inorganic synthesis identifying program can be employed recursively to convert a desired reactant combination in a multistep process to yield a target inorganic material β, as shown in FIG. 5. In this manner, where a reactant is not directly or commercially available to prepare the target, the reactant becomes an intermediate in a multistep synthesis.

In other aspects of the invention, cost can be considered in the selection of starting materials/precursors and bias the recommendations from the inorganic synthesis identifying program. Other factors that can be considered to bias the recommendations are to avoid certain reactants, elemental phases, or alloys, and such filters can be input by the user. For example, peroxides or superoxides can be avoided or explicitly included, based on user instruction. System can be instructed to use subclasses of starting materials/precursors such as carbonates, nitrates etc. The program can also bias the recommendation based on the oxidation state of the atoms in the target inorganic material and the reactant(s) from which it is synthesized, for example the recommendation can be where similar oxidation states of reactants and products are favored. The program can be biased for carbothermal synthetic conditions for the preparation of ceramics.

The program can allow the inclusion of catalysts for the synthetic transformations. Unreactive materials towards the reagents that are epitaxially matching with the target inorganic material can be included for this purpose. Catalysts can be determined by a non-reactivity exhibited by a direct tie-lines between reagent phases and the nucleation agent (catalyst) and the target inorganic material phase and the nucleation agent. Co-precipitation with the target inorganic material can be allowed where purity of the target inorganic material is not a requirement.

Figure 6:
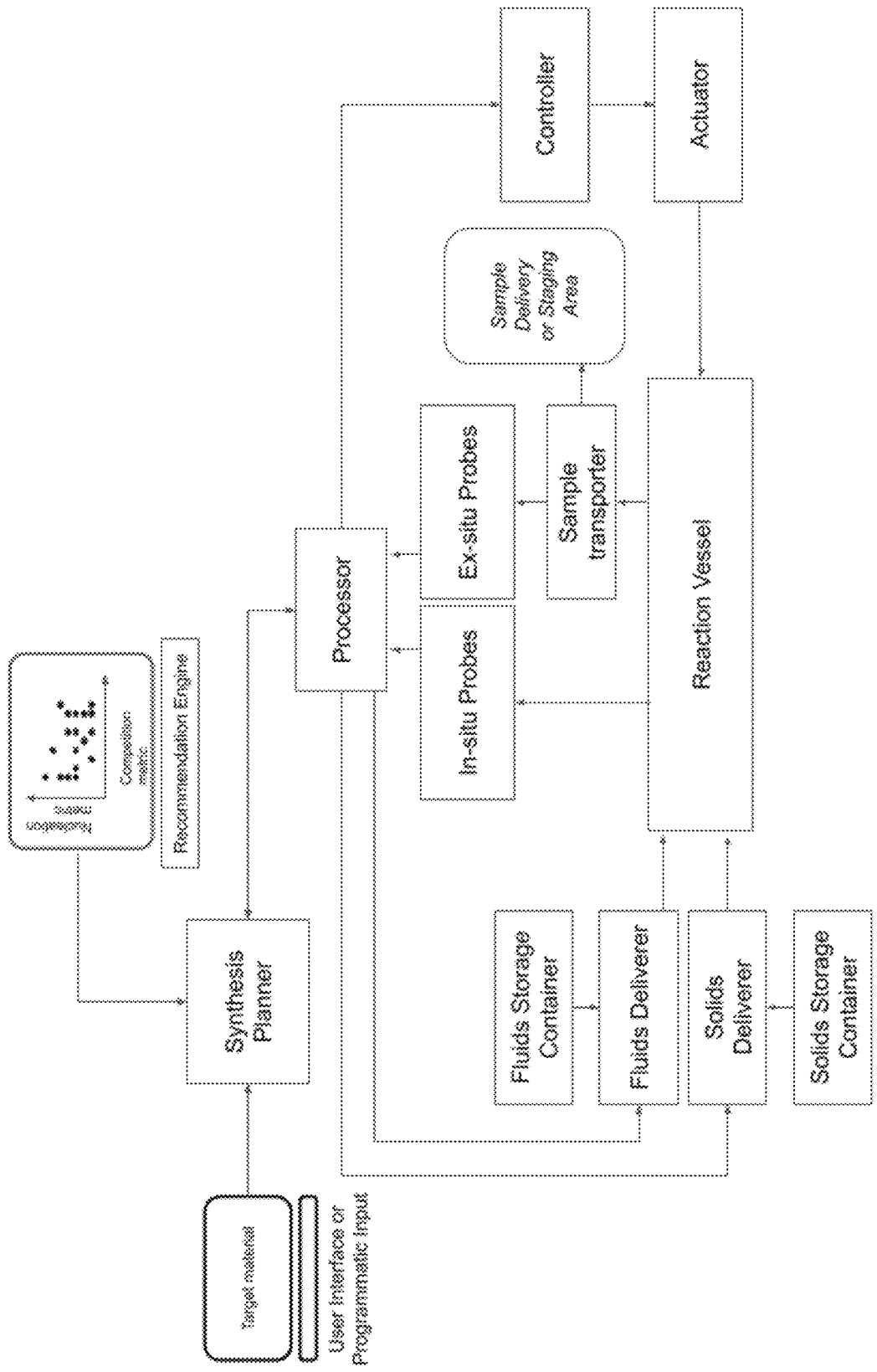
FIG. 6 is a diagram of the synthesis machine.

The output recommended syntheses are used as the input to direct the synthesis machine for robotic synthesis of the target inorganic material and are received by the synthesis planner module of the synthesis machine. In such a synthesizer, components for the delivering of the identified inorganic reactants and any catalysts, their combining as solids and gases, and recovering the target inorganic material are linked. As shown in FIG. 6 the Synthesis planner is coupled to a processor, which is connected to reactant sources, delivery devices, controllers, actuators, and probes. The processor outputs a signal to a solids deliverer to provide a desired quantity of a solid reactant that can be coupled to a reactant storage container. The solid reactants can be in powder or granular form. Although one solids delivery device is illustrated in FIG. 6, there can be one, two, or more solids delivery devices connected to one, two, or more solids storage containers in the synthesis machine. The delivery device provides the quantity prescribed by the synthesis planner computer program to the reaction vessel. The processor can also control a valve or other fluid deliverer to transfer a gas to the reaction vessel. The gas can be for pacification, dilution or as a reactant (e.g. $O_2$). Again, although one fluids delivery device is illustrated in FIG. 6, there can be one, two, or more fluids delivery devices connected to one, two, or more fluids storage containers in the synthesis machine. The processor outputs a signal to a controller that provides a signal to actuators that provide or remove heat, pressure, or provide radiation. The processor receives input from probes connected to or in communication with the reaction vessel and makes these signals available to the synthesis planner.

A first reactant is delivered to a reaction site that can be in a volume in a portion of a reaction vessel, where the vessel can be inert or made of a second reactant for the synthesis of the target inorganic material. Addition of the reactants are by dispensers that are, for example, powder dispensers, micropipettes adapted to deliver solid powders alone or as a suspension in a readily removed solvent by moderate heating or by reduction of pressure on the vessel. Another method that can allow the delivery of the reactants, when carried out at microgram levels, is by ink-jet printing techniques, where the solids are delivered in a vehicle that is readily removed from the vessel. Other techniques that can be employed are spray pyrolysis techniques; laser ablation techniques; electron beam or thermal evaporation techniques; doping techniques; and chemical vapor deposition techniques and gas flowing techniques.

The reaction vessel can contain components for the effective mixing, grinding and milling of the reactants, reaction mixture and any needed catalyst for the solid-state reaction, for example, the vessel can be the containment portion of a ball mill where the first reactant and second reactant are milled together to generate the target inorganic material of an intermediate material in a multistep synthesis. The temperature of the vessel can be lowered by instructing the controller to facilitate milling process more effectively.

The vessel can be evacuated and/or configured to receive an over gas through one or more valves. The gas can be inert, or the gas can be a reagent. The vessel can be configured to remove a gas generated by the reaction through a valve to drive a reaction towards products and/or maintain a constant pressure, which can be automatically instructed as such by the planner if attempted synthesis reaction is expected to evolve gas as received from the recommender system (e.g. for removal of evolving $CO_2$).

Using these components, desired temperatures, pressures, and radiant energies can be provided to the reactant(s) and any included catalysts to control the reaction conditions. The mode of controlling the reaction conditions can be by using a heater, a chiller, a pressurizer, such as a piston, vacuum pump for evacuation of the vessel chamber, or a radiator of laser, infrared, visible, or ultraviolet radiation.

The synthesis machine can have in-situ and ex-situ probes for analysis of the reaction, reaction intermediates, and targeted inorganic material products. Probes for temperature, pressure and mass can be implemented in-situ (coupled to the vessel and/or the vessel cap), whereas structure, composition, and calorimetry probes can be implemented as ex-situ probes, to which a small part of the sample can be transferred by an automated sample transporter coupled to the vessel. The probes can perform analyses of various types to monitor the reaction conditions, reactant compositions, extent of reaction, and composition, structure, identity and purity of the product inorganic material or any precipitating byproduct. In-situ probes can include: balances; thermal gauges; thermometers; thermocouples; pressure gauges; optical digital cameras; infrared cameras; and ex-situ probes can include: diffractometers, such as X-ray diffractometers; spectroscopic devices, such as Energy-dispersive Spectroscopy or X-ray Fluorescence Spectroscopy; calorimetric scanners, such as a Differential Scanning calorimetry; optical and electron microscopes, and any other probes, to keep track of phases and reaction stages, as well as characterize the structural and thermal aspects of the reactants and products.

Calorimetric analysis of the reactants delivered by the solid deliverers or any intermediate product can be performed individually prior to mixing of reactants for a synthesis reaction to analyze automatically and obtain a highest attainable temperature for each solid reactant without the exhibition of any notable phase transformation or decomposition. The highest attainable temperature values of all reactants of a reaction can be stored. The lowest temperature for a reaction can be instructed by the synthesis planner to the controller and set as the targeted nominal reaction temperature for the attempted reaction. Likewise, a ceiling temperature that should not be crossed can be instructed by the synthesis planner to the controller. The synthesis planner can instruct the system to run reactions at the highest temperature where the solid reactants does not exhibit a pronounced transformation or decomposition to any other phase. This determined reaction temperature can be used to instruct the recommender system to regenerate recommendations and validate that the reaction under consideration should be characterized as favorable at the determined temperature. This iterative process can be carried out between the synthesis planner and the recommender until a degree of confidence in the selected reaction's nominal temperature is reached. Decomposition temperatures for common precursors, such as, metal oxides, nitrates, carbonates, and hydroxides, can be stored in memory or a database of the synthesis planner and used directly in leu of any explicit measurement. For intermediates or starting materials for which such temperature information does not exist, the synthesis planner can instruct acquisition of these decomposition temperatures and store them in memory or a database for subsequent use.

If the synthesis planner module receives more than one recommended reaction for the synthesis of the target material, such as equally plausible reactions that are on or near the Pareto frontier of the recommendation plots, the synthesis planner may further refine and prioritize this preliminary recommended subset to form a shorter ranked ordered list of synthesis reactions to attempt. Ranking can be based on the prioritization of one metric, such as the competition metric of the preliminary recommended reactions, or on the basis of a rank aggregation, for example, using the average rank of the target reaction when the preliminary recommended viable reactions on or near the Pareto frontier are sorted on the basis of their nucleation and competition metrics independently. The synthesis planner can request inspection from a user to monitor the reaction planning and request adjustments or confirmation before execution.

During execution of a reaction at a target temperature, periodically the synthesis planner can instruct the controller to initiate in-situ and ex-situ probes for determination of the extent of the reaction and/or the formation of the target material and its purity. On the basis of this input, the synthesis planner may instruct the controller to cool the vessel for remixing and regrinding to expose fresh reactant surfaces and to reheat the vessel to the reaction temperature. This process can be repeated periodically, for example in intervals of 2, 5, 10 or 24 hours of high-temperature annealing followed by probing, and, if needed, regrinding and mixing. After a prescribed number of iterations, if the system cannot isolate or detect the emergence of the target inorganic material, the planner may instruct the current synthesis to halt, and initiate the process for the next ranked reaction when available. If the desired target inorganic material or a desired intermediate that would be used subsequently for preparation of a target material is obtained, the sample is transferred to a target material's sample delivery or to a staging area of an intermediate for a subsequent or ultimate target inorganic material. The staging area is an atmosphere and humidity-controlled container where the reaction intermediate for a planned multi-step synthesis can be stored and returned to the vessel when needed.

Current high-throughput combinatorial synthesis technologies explore multiple compositions simultaneously without targeted control on the product materials. In contrast, the synthesis machine described here is not designed for high-throughput with a multiplicity of reactions carried out in parallel designed to screen a host of compositions. Rather, the synthetic machine is directed by a planner that is coupled to the recommendation program and is designed to incrementally perform a series of reactions that ultimately form a targeted inorganic material. The synthetic machine can continuously or incrementally add and mix reactants in a series of steps based on the recommended routes in the reaction vessel.

Common reagent or other grade reactants, such as, metals, metal alloys, metal oxides, carbonates, nitrates, nitrides, phosphates, and hydroxides for multiple target inorganic materials can be stored in containers that are available for delivery to the reaction vessel as directed by the instructions from the computer processor to actuators. Other storage containers can be filled with reagents for a target inorganic material by a technician. Storage containers can be atmosphere and humidity controlled. Storage containers having various dimensions and configurations can be employed, for example, one that is in the form of an ink-jet cartridge for a solid particle suspension in a volatile solvent, to be delivered as a reagent. The storage containers can be available from reagent suppliers in this form. The storage containers can have delivery paths that are coupled to grinders or mills and/or other solids processing components that refine the solid reagent into an appropriate size and form for the reaction prescribed by the controlling computer program.

Any kind of processing system or another apparatus adapted for carrying out the methods described herein can be employed. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product that comprises all the features enabling the implementation of the methods described herein and, which when loaded in a processing system, is able to carry out these methods.

Hardware arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a hard disk drive (HDD), a solid-state drive (SSD), a read-only memory (ROM), an erasable programmable read-only memory, a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain or store a program for use by or in connection with an instruction execution system, apparatus, or device.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or processor. In the latter scenario, the remote computer may be connected to the user's computer through any type of network, including a local area network (LAN) or a wide area network (WAN), or the connection may be made to an external computer (for example, through the Internet using an Internet Service Provider).

Generally, "module," as used herein, includes routines, programs, objects, components, data structures, and so on that perform tasks or implement data types. In further aspects, a memory generally stores the noted modules. The memory associated with a module may be a buffer or cache embedded within a processor, a RAM, a ROM, a flash memory, or another suitable electronic storage medium. In still further aspects, a module may be implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

Various aspects of the present disclosure are further illustrated with respect to the following Examples. It is to be understood that these Examples are provided to illustrate specific embodiments of the present disclosure and should not be construed as limiting the scope of the present disclosure in or to any aspect.

The headings (such as "Background" and "Summary") and sub-headings used herein are intended only for general organization of topics within the present disclosure and are not intended to limit the disclosure of the technology or any aspect thereof. The recitation of multiple embodiments having stated features is not intended to exclude other embodiments having additional features, or other embodiments incorporating different combinations of the stated features.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes examples, the true scope of the disclosure should not be so limited since other modifications will become apparent to the skilled practitioner upon a study of the specification and the following claims. Reference herein to one aspect, or various aspects means that a feature, structure, or characteristic described in connection with an embodiment or system is included in at least one embodiment or aspect. The appearances of the phrase "in one aspect" (or variations thereof) are not necessarily referring to the same aspect or embodiment. It should be also understood that the various method steps discussed herein do not have to be carried out in the same order as depicted, and not each method step is required in each aspect or embodiment.

The foregoing description of the embodiments has been provided for purposes of illustration and description. It is not intended to be exhaustive or to limit the disclosure. Individual elements or features of any given embodiment are generally not limited to that embodiment, but, where applicable, are interchangeable and can be used in a selected embodiment, even if not specifically shown or described. The same may also be varied in many ways. Such variations should not be regarded as a departure from the disclosure, and all such modifications are intended to be included within the scope of the disclosure.

What is claimed is:

1. A synthesis machine for preparation of a target inorganic material, comprising:
  a synthesis planner module coupled with a processor that outputs from a synthesis route recommendation computer program at least one solid-state synthetic method for the preparation of the target inorganic material, where the at least one solid-state synthetic method comprises a viable subset of a multiplicity of possible synthetic reactions;
  at least one reaction vessel for containment of at least one reactant for formation of the target inorganic material, wherein each reaction vessel is for the performance of a single solid-state synthetic method under a first stoichiometry and a first set of conditions contained in the output of the computer program, or as an enumerated stoichiometry and enumerated set of conditions modified according to a result of a previous preparation of the target inorganic material by the synthesis machine, ultimately resulting from the first stoichiometry and the first set of conditions;

at least one delivery mechanism to provide a plurality of reactants to the at least one reaction vessel, wherein a quantity of each of the plurality of reactants is provided at the first stoichiometry or in the enumerated stoichiometry;

at least one controller configured for:
controlling the first set of conditions or the enumerated set of conditions required for the at least one solid-state synthetic method;
monitoring the first set of conditions or the enumerated set of conditions during the at least one solid-state synthetic method; and
evaluating a progress of a reaction of the at least one solid-state synthetic method.

2. The synthesis machine according to claim 1, wherein the at least one solid-state synthetic method from the viable subset of the multiplicity of possible synthetic reactions includes at least one recommended synthesis with a calculated nucleation barrier metric and a competition metric that resides at or near an origin of a plot of the nucleation barrier metric versus the competition metric or is on or near a pareto frontier of the plot for the target inorganic material input by a user, and wherein each of the at least one recommended synthesis is separately input to the synthesis machine for syntheses.

3. The synthesis machine according to claim 1, wherein the computer program comprises at least one interface for input of the target inorganic material by a user and/or by an inputting computer program.

4. The synthesis machine according to claim 1, wherein the delivery mechanism is computer controlled.

5. The synthesis machine according to claim 1, wherein the delivery mechanism comprises one or more of a powder dispensing technique, pipetting technique, ink-jet printing technique, spray pyrolysis technique, laser ablation technique, thermal evaporation technique; doping technique, chemical vapor deposition technique and gas flowing technique.

6. The synthesis machine according to claim 1, wherein the controller is coordinated with the synthesis planning module and imposes one or more reaction conditions according to the synthesis planner module with a signal imposed upon one or more of a heater, chiller, pressurizer, vacuum pump, and irradiators of laser, infrared, visible, or ultraviolet radiation.

7. The synthesis machine according to claim 1, wherein the controller coordinates monitoring of at least one in-situ probe of a thermistor, thermocouple, pressure gauge, balance, and an infrared camera attached to the reaction vessel, wherein a temperature, pressure, reaction mass, and visual depiction of a reaction mixture in the vessel are output to the processor.

8. The synthesis machine according to claim 1, wherein the controller coordinates monitoring one or more of temperature, pressure, mass, and ex-situ probes including diffractometers (such as an X-ray diffractometer), spectroscopic devices (such as an energy-dispersive spectroscopy device or X-ray fluorescence spectroscopy), calorimetric scanners (such as a differential scanning calorimetry), and optical or electron microscopes, results of which are output to synthesis planner's coupled processor.

9. The synthesis machine according to claim 1, further comprising a robotic sample transporter coupled to the controller for transporting a defined amount of a reaction mixture to one or more an ex-situ probe selected from a diffractometer, spectroscopic device, calorimetric scanner, optical microscope, or electron microscope.

10. A synthesis machine for preparation of a target inorganic material, comprising:
a synthesis planner module coupled with a processor that outputs from a synthesis route recommendation computer program:
at least one solid-state synthetic method for the preparation of the target inorganic material, where the at least one solid-state synthetic method comprises a viable subset of a multiplicity of possible synthetic reactions;
at least one recommended synthesis from the at least one solid-state method, the at least one recommended synthesis being a synthesis with a calculated nucleation barrier metric and a competition metric that resides at or near an origin of a plot of the nucleation barrier metric versus the competition metric or is on or near a pareto frontier of the plot for the target inorganic material input by a user, and wherein the at least one recommended synthesis is separately input to the synthesis machine for syntheses;
at least one reaction vessel for containment of at least one reactant for formation of the target inorganic material, wherein each reaction vessel is for the performance of a single recommended synthesis under a first stoichiometry and a first set of conditions contained in the output of the computer program, or as an enumerated stoichiometry and enumerated set of conditions modified according to a result of a previous preparation of the target inorganic material by the synthesis machine, ultimately resulting from the first stoichiometry and a first set of conditions;
at least one delivery mechanism to provide a plurality of reactants to the reaction vessel, wherein a quantity of each of the plurality of reactants is provided at the first stoichiometry or in the enumerated stoichiometry;
at least one controller configured for:
controlling the first set of conditions or the enumerated set of conditions required for the at least one recommended synthesis;
monitoring the first set of conditions or the enumerated set of conditions during the at least one recommended synthesis; and
evaluating a progress of a reaction of the at least one recommended synthesis.

11. The synthesis machine according to claim 10, wherein the computer program comprises at least one interface for input of the target inorganic material by a user and/or by an inputting computer program.

12. The synthesis machine according to claim 10, wherein the delivery mechanism is computer controlled.

13. The synthesis machine according to claim 10, wherein the delivery mechanism comprises one or more of a powder dispensing technique, pipetting technique, ink-jet printing technique, spray pyrolysis technique, laser ablation technique, thermal evaporation technique; doping technique, chemical vapor deposition technique, and gas flowing technique.

14. The synthesis machine according to claim 10, wherein the controller is coordinated with the synthesis planning module and imposes one or more reaction conditions according to the synthesis planner module with a signal imposed upon one or more of a heater, chiller, pressurizer, vacuum pump, and irradiators of laser, infrared, visible, or ultraviolet radiation.

15. The synthesis machine according to claim 10, wherein the controller coordinates monitoring of at least one in-situ probe of a thermistor, thermocouple, pressure gauge, balance, and an infrared camera attached to the reaction vessel, wherein a temperature, pressure, reaction mass, and visual depiction of a reaction mixture in the vessel are output to the processor.

16. The synthesis machine according to claim 10, wherein the controller coordinates monitoring one or more of temperature, pressure, mass, and ex-situ probes including diffractometers (such as an X-ray diffractometer), spectroscopic devices (such as an energy-dispersive spectroscopy device or X-ray fluorescence spectroscopy), calorimetric scanners (such as a differential scanning calorimetry), and optical or electron microscopes, results of which are output to synthesis planner's coupled processor.

17. The synthesis machine according to claim 10, further comprising a robotic sample transporter coupled to the controller for transporting a defined amount of a reaction mixture to one or more an ex-situ probe selected from a diffractometer, spectroscopic device, calorimetric scanner, optical microscope, or electron microscope.

* * * * *